United States Patent
Toporek et al.

(10) Patent No.: US 11,406,459 B2
(45) Date of Patent: Aug. 9, 2022

(54) ROBOTIC INSTRUMENT GUIDE INTEGRATION WITH AN ACOUSTIC PROBE

(71) Applicant: KONINKLIJKE PHILIPS N.V., Eindhoven (NL)

(72) Inventors: Grzegorz Andrzej Toporek, Boston, MA (US); Aleksandra Popovic, Boston, MA (US); Sean Joseph Kyne, Brookline, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 204 days.

(21) Appl. No.: 16/628,719

(22) PCT Filed: Jul. 5, 2018

(86) PCT No.: PCT/EP2018/068315
§ 371 (c)(1),
(2) Date: Jan. 6, 2020

(87) PCT Pub. No.: WO2019/008127
PCT Pub. Date: Jan. 10, 2019

(65) Prior Publication Data
US 2020/0188041 A1     Jun. 18, 2020

Related U.S. Application Data

(60) Provisional application No. 62/529,634, filed on Jul. 7, 2017.

(51) Int. Cl.
*A61B 34/30* (2016.01)
*A61B 8/00* (2006.01)
(Continued)

(52) U.S. Cl.
CPC .......... *A61B 34/30* (2016.02); *A61B 8/4245* (2013.01); *A61B 8/4455* (2013.01);
(Continued)

(58) Field of Classification Search
CPC ........ A61B 17/3403; A61B 2017/3407; A61B 2017/3409; A61B 2017/3413;
(Continued)

(56) References Cited

U.S. PATENT DOCUMENTS

| 2,906,569 A | 9/1959 | Runton |
| 6,124,710 A | 9/2000 | Kordecki |

(Continued)

FOREIGN PATENT DOCUMENTS

| EP | 3037660 | 6/2016 |
| WO | 2009/063360 | 5/2009 |

(Continued)

OTHER PUBLICATIONS

International Search Report and Written Opinion dated Oct. 12, 2018 for International Application No. PCT/EP2018/068315 filed Jul. 5, 2018.

*Primary Examiner* — Michael T Rozanski

(57) ABSTRACT

A robotic acoustic probe for application with an interventional device (60). The robotic acoustic probe employs an acoustic probe (20) including a imaging platform (21) having a device insertion port (22) defining a device insertion port entry (23) and device insertion port exit (24), and further including an acoustic transducer array (25) are disposed relative the device insertion port exit (24). The robotic acoustic probe further employs a robotic instrument guide (40) including a base (41) mounted to the imaging platform (21) relative to the device insertion port entry (23), and an end-effector (45) coupled to the base (41) and transitionable between a plurality of poses relative to a
(Continued)

remote-center-of-motion (49). The end-effector (45) defines an interventional device axis (48) extending through the device insertion port (22), and the remote-center-of-motion (49) is located on the interventional device axis (48) adjacent the device insertion port exit (24).

20 Claims, 9 Drawing Sheets

(51) Int. Cl.
  *A61B 90/50* (2016.01)
  *A61B 17/34* (2006.01)
  *A61B 34/20* (2016.01)

(52) U.S. Cl.
  CPC .......... *A61B 17/3403* (2013.01); *A61B 90/50* (2016.02); *A61B 34/20* (2016.02); *A61B 2017/3413* (2013.01); *A61B 2034/2063* (2016.02)

(58) Field of Classification Search
  CPC .... A61B 2034/2051; A61B 2034/2055; A61B 2034/2061; A61B 2034/2063; A61B 2090/378; A61B 34/20; A61B 34/30; A61B 34/32; A61B 8/0841; A61B 8/4227; A61B 8/4245; A61B 8/4455; A61B 90/50
  See application file for complete search history.

(56) References Cited

U.S. PATENT DOCUMENTS

| | | | |
|---|---|---|---|
| 6,911,008 | B2 | 6/2005 | Pelissier |
| 7,476,050 | B2 | 1/2009 | Ditzler |
| 7,482,575 | B2 | 1/2009 | Sidor |
| 8,934,003 | B2 | 1/2015 | Popovic |
| 2005/0027193 | A1 | 2/2005 | Mitschke |
| 2009/0041565 | A1 | 2/2009 | Rodriguez |
| 2015/0065916 | A1 | 3/2015 | Maguire |
| 2017/0165847 | A1 | 6/2017 | Popovic |

FOREIGN PATENT DOCUMENTS

| | | |
|---|---|---|
| WO | 2016/154714 | 10/2016 |
| WO | 2017/114701 | 7/2017 |
| WO | 2017/114956 | 7/2017 |

ROBOTIC INSTRUMENT GUIDE INTEGRATION WITH AN ACOUSTIC PROBE

CROSS REFERENCE TO RELATED APPLICATIONS

This application is the U.S. National Phase application under 35 U.S.C. § 371 of International Application No. PCT/EP2018/068315 filed Jul. 5, 2018, published as WO 2019/008127 on Jan. 10, 2019, which claims the benefit of U.S. Provisional Patent Application No. 62/529,634 filed Jul. 7, 2017. These applications are hereby incorporated by reference herein.

FIELD OF THE INVENTION

The inventions of the present disclosure generally relate to acoustic guidance of a robotically controlled interventional device (e.g., ultrasound guidance of a robotically controlled needle, introducer, scope, etc.).

The inventions of the present disclosure more particularly relate to an integration of a robotic instrument guide with an acoustic probe for an enhanced acoustic guidance of a robotically controlled interventional device.

BACKGROUND OF THE INVENTION

In ultrasound-guided percutaneous needle biopsies, targeting challenging lesions may be time consuming. Tight time constrains may be predominately critical to puncture lesions that are either located deeply in the organ or close to the critical anatomical structures, or both. Such lesions may involve out-of-plane, oblique needle trajectories thus challenging a practitioner to demonstrate good hand-eye coordination as well as imaging skills required to constantly keep the needle in the field of view. A large-field-of-view ultrasound volumetric image may be potentially practical for the out-of-plane needle trajectories as well as better understanding of the intra-operative situation. Furthermore, robotic control of the needle integrated with the large-field-of view ultrasound may be potentially practice for a revolution about the needle about a skin entry point and/or a translation of the needle within the skin entry point.

SUMMARY OF THE INVENTION

The inventions of the present disclosure provide for a robotic acoustic probe having a remote center of motion (RCM) locatable at a skin-entry point of a patient anatomy for more intuitive and safer interventional procedures.

One embodiment of the inventions of the present disclosure is a robotic acoustic probe employing an acoustic probe and a robotic instrument guide.

The acoustic probe includes an imaging platform having a device insertion port defining a device insertion port entry and device insertion port exit, and further including an acoustic transducer array disposed relative to the device insertion port exit (e.g., the acoustic transducer array encircling the device insertion port exit).

The robotic instrument guide includes a base mounted to the imaging platform relative to the device insertion port entry, and further includes an end-effector coupled to the base and transitionable between a plurality of instrument poses relative to a remote center of motion.

The end-effector defines an interventional device axis extending through the device insertion port, and the remote center of motion is located on the interventional device axis adjacent the device insertion port exit.

A second embodiment of the inventions of the present disclosure is a robotic acoustic system employing the aforementioned embodiment of the robotic acoustic probe and further employing an robotic instrument guide controller for controlling a transitioning of the end-effector between the plurality of instrument poses relative to the remote center of motion.

The transitioning of the end-effector between the plurality of instrument poses relative to the remote center of motion may include a revolution of the end-effector about the remote center of motion and/or a translation of the end-effector along the interventional device axis.

The robotic instrument guide controller may derive the control of the transitioning of the end-effector between the plurality of instrument poses relative to the remote center of motion from an ultrasound volumetric imaging of a patient anatomy by the acoustic transducer array, a modality volumetric imaging of the patient anatomy by an imaging modality and/or a position tracking of the robotic instrument guide within a tracking coordinate system.

A third embodiment of the inventions of the present disclosure is an interventional method utilizing the aforementioned embodiment of the robotic acoustic probe.

The interventional method involves a positioning of the robotic acoustic probe relative to a skin entry point of a patient anatomy, wherein the remote center of motion coincides with the skin entry port.

Subsequent thereto, the interventional method further involves an ultrasound volumetric imaging of the patient anatomy by the acoustic transducer array, and/or a transitioning of the end-effector between the plurality of instrument poses relative to the remote center of motion.

For purposes of describing and claiming the inventions of the present disclosure:

(1) terms of the art of the present disclosure including, but not limited to, "acoustic transducer", "port", "pose", "arms" "arcs", "revolute joints", "end-effector" and "volumetric imaging" are to be understood as known in the art of the present disclosure and exemplary described in the present disclosure;

(2) the term "acoustic probe" broadly encompasses all acoustic probes, as known in the art of the present disclosure and hereinafter conceived, structurally arranged with an acoustic transducer array positioned relative to a device insertion port for inserting an interventional device within a patient anatomy;

(3) the term "imaging platform" broadly encompasses any type of structure supporting a positioning of the acoustic probe for an ultrasound volumetric imaging of an object by the acoustic transducer array. Examples of an imaging platform include a substrate, a CMUT and a probe handle (4) the term "acoustic transducer array" broadly encompasses any type of arrangement of a plurality of acoustic transducers for an ultrasound volumetric imaging of an object within a field of view of the acoustic transducers;

(5) the term "robotic instrument guide" broadly encompasses all instrument guides, as known in the art of the present disclosure and hereinafter conceived, structurally arranged with two or more revolute joints having rotational axes that intersect at a remote center of motion (RCM);

(6) the term "adjacent" as related to a remote center of motion and a device insertion port exit broadly encompasses an spatial positioning of the remoter center of motion and the device insertion port exit whereby the remote center of motion may coincide with a skin entry point of a patient anatomy including the remote center of motion being internal to the device insertion port adjacent the device insertion port, the remote center of motion lying within a plane of the device insertion port exit and the remote center of motion being external to the device insertion port adjacent the device insertion port.

(7) the term "interventional device" is to be broadly interpreted as known in the art of the present disclosure including interventional device known prior to and conceived after the present disclosure. Examples of an interventional device include, but are not limited to, vascular interventional tools (e.g., guidewires, catheters, stents sheaths, balloons, atherectomy catheters, IVUS imaging probes, deployment systems, etc.), endoluminal interventional tools (e.g., endoscopes, bronchoscopes, etc.) and orthopedic interventional tools (e.g., k-wires and screwdrivers);

(8) the term "interventional imaging system" broadly encompasses all imaging systems, as known in the art of the present disclosure and hereinafter conceived, for pre-operatively and/or intra-operatively imaging a patient anatomy during an interventional procedure. Examples of an interventional imaging system include, but is not limited to, a stand-alone x-ray imaging system, a mobile x-ray imaging system, an ultrasound volumetric imaging system (e.g., TEE, TTE, IVUS, ICE), a computed tomography ("CT") imaging system (e.g., a cone beam CT), a positron emission tomography ("PET") imaging system and a magnetic resonance imaging ("MRI") system;

(9) the term "position tracking system" broadly encompasses all tracking systems, as known in the art of the present disclosure and hereinafter conceived, for tracking a position (e.g., a location and/or an orientation) of an object within a coordinate space. Examples of a position measurement system include, but is not limited to, an electromagnetic ("EM") measurement system (e.g., the Auora® electromagnetic measurement system), an optical-fiber based measurement system (e.g., Fiber-Optic RealShape™ ("FORS") measurement system), an ultrasound measurement system (e.g., an InSitu or image-based US measurement system), an optical measurement system (e.g., a Polaris optical measurement system), a radio frequency identification measurement system and a magnetic measurement system;

(10) the term "controller" broadly encompasses all structural configurations of an application specific main board or an application specific integrated circuit for controlling an application of various inventive principles of the present disclosure as exemplary described in the present disclosure. The structural configuration of the controller may include, but is not limited to, processor(s), computer-usable/computer readable storage medium(s), an operating system, application module(s), peripheral device controller(s), interface(s), bus(es), slot(s) and port(s). A descriptive label as used herein for a particular controllers of the present disclosure distinguishes for identification purposes the particular controller as described and claimed herein from other controller(s) without specifying or implying any additional limitation to the term "controller";

(11) the term "application module" broadly encompasses a component of an controller consisting of an electronic circuit and/or an executable program (e.g., executable software and/or firmware stored on non-transitory computer readable medium(s)) for executing a specific application. A descriptive label as used herein for a particular application module of the present disclosure distinguishes for identification purposes the particular application module as described and claimed herein from other application module(s) without specifying or implying any additional limitation to the term "application module"; and

(12) the terms "signal", "data" and "command" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Signal/data/command communication between various components of the present disclosure may involve any communication method as known in the art of the present disclosure including, but not limited to, signal/data/command transmission/reception over any type of wired or wireless datalink and a reading of signal/data/commands uploaded to a computer-usable/computer readable storage medium. A descriptive label as used herein for a particular signal/data/command of the present disclosure distinguishes for identification purposes the particular signal/data/command as described and claimed herein from other signal(s)/data/command(s) without specifying or implying any additional limitation to the term the terms "signal", "data" and "command".

The foregoing embodiments and other embodiments of the inventions of the present disclosure as well as various features and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

To facilitate an understanding of the various inventions of the present disclosure, the following description of FIGS.

1-6 teaches embodiments of robotic acoustic probes and robotic acoustic systems in accordance with the inventive principles of the present disclosure. From this description, those having ordinary skill in the art will appreciate how to practice various and numerous embodiments of robotic acoustic probes and robotic acoustic systems in accordance with the inventive principles of the present disclosure.

Also from this description, those having ordinary skill in the art will appreciate an incorporation of a robotic acoustic system of the present disclosure in numerous and various types of a robotically controlled image-guided interventions utilizing a robotic acoustic guide of the present disclosure.

Examples of such image-guided intervention include, but is not limited to:

1. image-guided interventional radiology procedures involving elongated interventional instruments (e.g., irreversible electroporation of the hepatic lesions, radiofrequency/microwave ablation, face joint injection, targeting of nerve blocks, percutaneous biopsies, etc. involving biopsy needles, ablation antennas, spinal needles, etc.);

2. interventions against structural heart diseases transapical involving introducer devices and closure device for a transapical access (e.g., a tricuspid valve-in-ring implantation, a transapical aortic valve replacement, a transapical transcatheter mitral valve implantation, etc.); and 3. laparoscopic procedures involving mini-laparoscopes, particularly for skin entry points of a diameter of approximately 3.5 mm (e.g., mini-laparoscopic cholecystectomy, mini-laparoscopic appendectomy, different types of mini-laparoscopic pediatric surgeries, mini-video assisted thoracic surgery, etc.).

Figure 1:
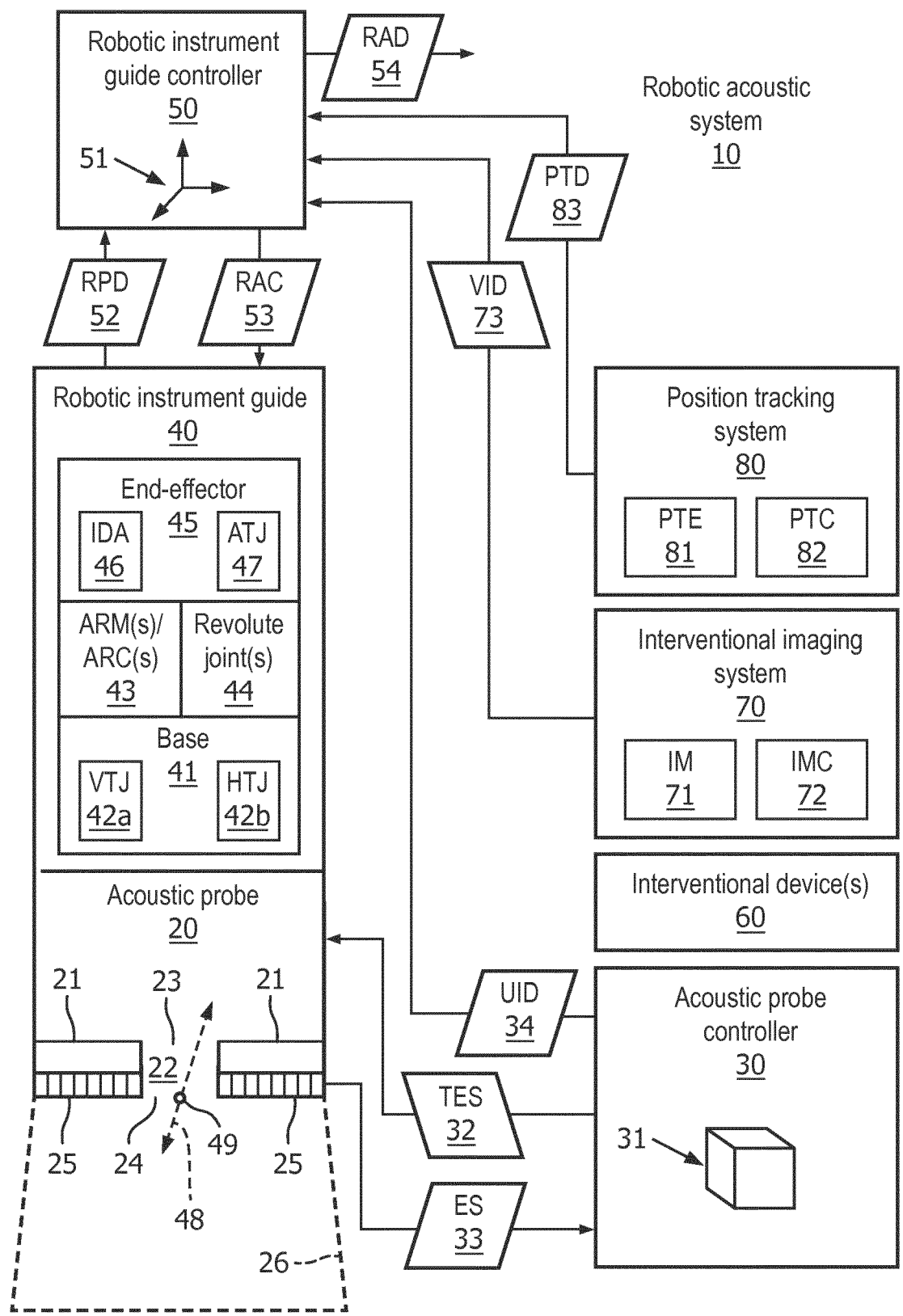
FIG. 1 illustrates an exemplary embodiment of a robotic acoustic system in accordance with the inventive principle of the present disclosure.

Referring to FIG. 1, a robotic acoustic system 10 of the present disclosure employs a robotic acoustic probe including an acoustic probe 20 and a robotic instrument guide 40 mounted onto acoustic probe 20.

Acoustic probe 20 has a structural arrangement of an imaging platform 21 having a device insertion port 22 having a device insertion port entry 23 and a device insertion port exit 24 for an insertion of an interventional device 60 as held by robotic instrument guide 40 along an instrument device axis 48 extending through device insertion port 22.

As will be further exemplary described in the present disclosure, in operation, robotic instrument guide 40 is mounted onto acoustic probe 20, such as, for example, by an attachment or a coupling of a base 41 of robotic instrument guide 40 to imaging platform 21 of acoustic probe 20. The mounting of guide 40 unto probe 20 establishes a location of a remote center of motion 49 of robotic instrument guide 40 along instrument device axis 48 adjacent the device insertion port exit 24 to thereby facilitate a coincidental alignment of remote center of motion 49 with a skin entry port into a patient anatomy.

In practice, imaging platform 21 and device insertion port 22 may have any geometrical shape, and imaging platform 21 may be any material composition suitable for any interventional procedure or for particular interventional procedure(s).

Also in practice, imaging platform 21 may have any configuration suitable for a mounting of base 41 of robotic instrument guide 40 unto imaging platform 21 as will be further described in the present disclosure.

Acoustic probe 20 further has a structurally arrangement of an acoustic transducer array 25 supported by imaging platform 21 and disposed relative to insertion port exit 23 for executing an ultrasound volumetric imaging of any object within a field of view 26 of acoustic transducer array 25. More particularly, as known in the art of the present disclosure, an acoustic probe controller 30 of system 10 communicates transducer excitation signals 32 to acoustic transducer array 25 to thereby energize acoustic transducer array 25 to transmit and receive ultrasound waves whereby acoustic probe 20 communicates echo data 33 to acoustic probe controller 30 for a generation of an ultrasound volumetric image 31 of any object within field of view 26.

In addition to facilitating a mounting of guide 40 onto probe 20, in practice, imaging platform 21 is structurally configured to manually or robotically position acoustic probe 20 for the ultrasound volumetric imaging of a patient anatomy by the acoustic transducer array 25. For example, imaging platform 21 may structurally be in the form of a substrate/CMUT positionable upon the patient anatomy, or a probe handle manually or robotically held on a patient anatomy.

In practice, acoustic transducer array 25 may include acoustic transceivers, or a subarray of acoustic transmitters and a subarray of acoustic receivers.

Figure 2A:
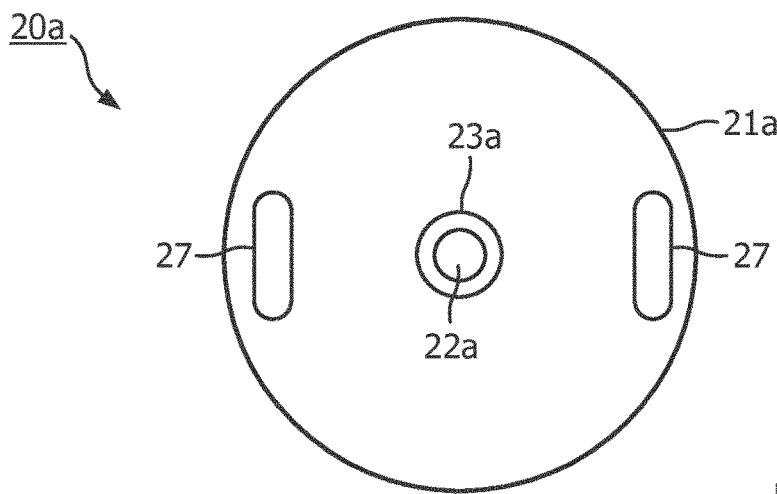
FIGS. 2A-2C illustrates a first exemplary embodiment of an acoustic probe in accordance with the inventive principle of the present disclosure.
Figure 2B:
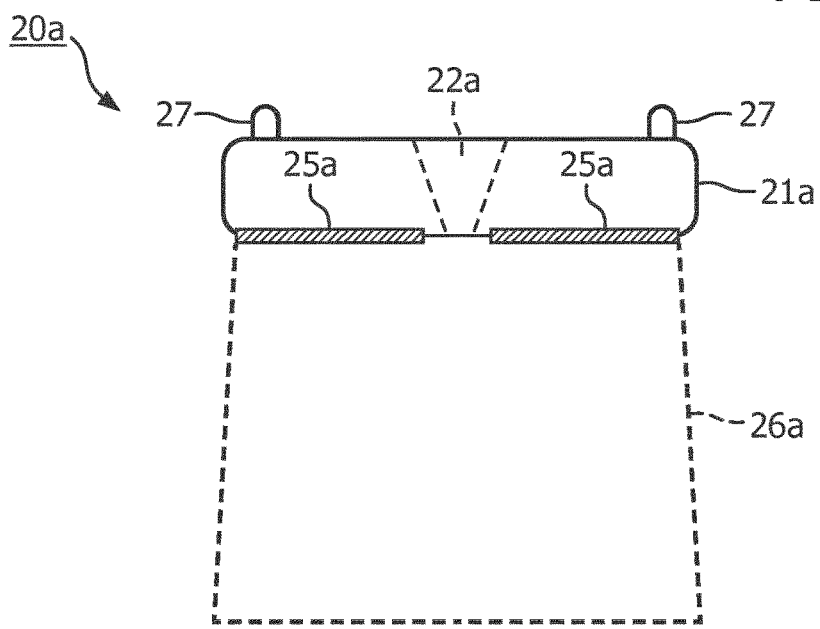
Figure 2C:
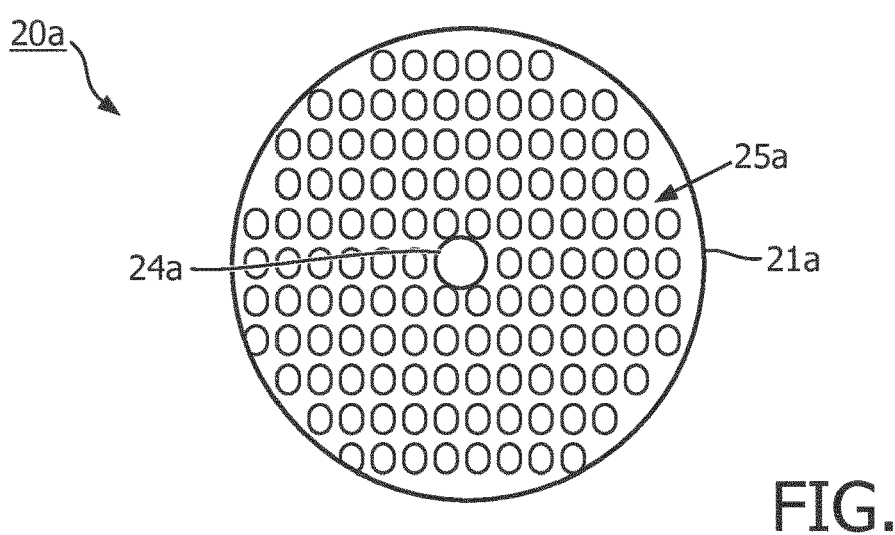

FIGS. 2A-2C illustrates an exemplary embodiment 20a of acoustic probe 20 (FIG. 1). Referring to FIGS. 2A-2C, acoustic probe 20a includes an imaging platform 21a in the form of a substrate constructed as a disc having a top surface shown in FIG. 2A and a bottom surface shown in FIG. 2C. A device insertion port 22a passes through imaging platform 21a and tapers from a circular device insertion point entry 23a formed on the top surface of imaging platform 21a to a circular device insertion port exit 24a formed on a bottom surface of imaging platform 21a.

An array 25a of acoustic transducers are supported on the bottom surface of imaging platform 21a and disposed around device insertion port exit 24a. Acoustic transducer array 25a may be energized as known in the art of the present disclosure to transmit and receive ultrasound waves within a field of view 26a of acoustic probe 20a.

A pair of hooks 27 are provided on a top surface of imaging platform 21a to facilitate a strapping of acoustic probe 20a around a patient.

Imaging platform 21a may support a mounting of a robotic instrument guide 40 (FIG. 1) via unique clips or locks embedded in imaging platform 21a.

Figure 3A:
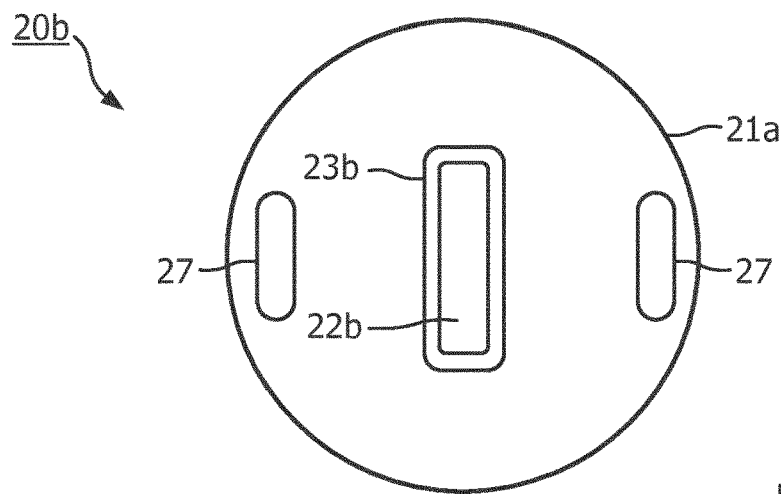
FIGS. 3A-3C illustrates a first exemplary embodiment of an acoustic probe in accordance with the inventive principle of the present disclosure.
Figure 3B:
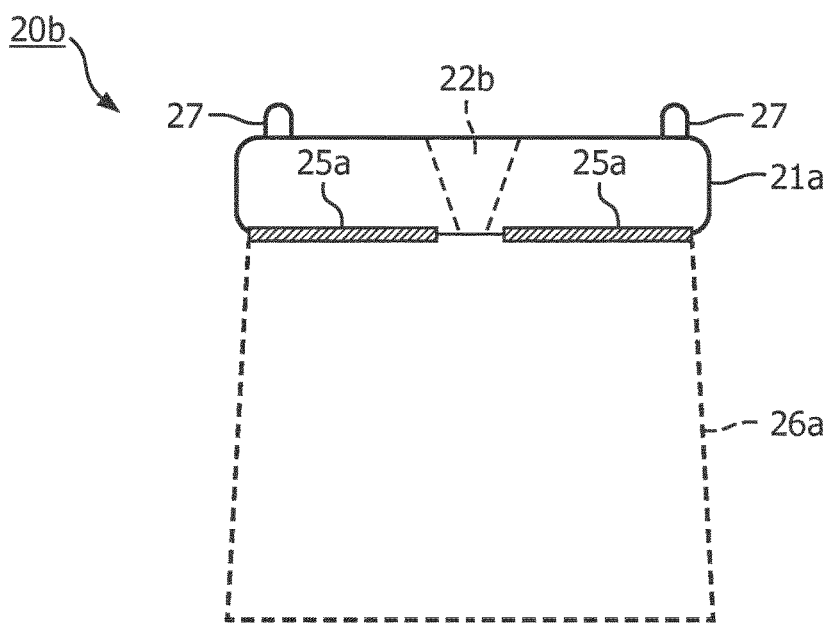
Figure 3C:
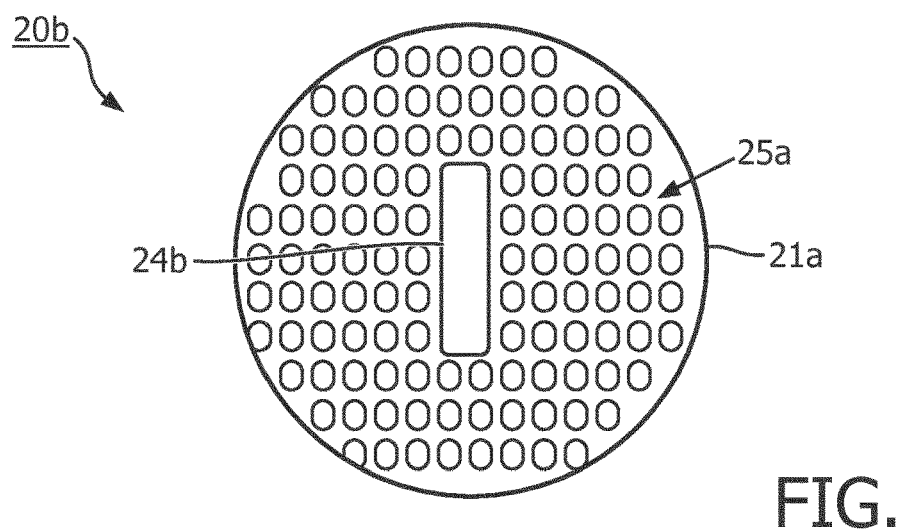

FIGS. 3A-3C illustrates a further exemplary embodiment 20b of acoustic probe 20 (FIG. 1). Referring to FIGS. 3A-3C, acoustic probe 20b is identical to acoustic probe 20a (FIGS. 2A-2C) with the exception a device insertion port 22b passing through imaging platform 21a and tapering from an elongated device insertion point entry 23b formed on the top surface of imaging platform 21a to an elongated device insertion port exit 24b formed on a bottom surface of imaging platform 21a.

Referring back to FIG. 1, robotic instrument guide 40 has a structural arrangement of a base 41, two (2) or more arms/arcs 43, (1) one or more revolute joints 44 and an end-effector 45 for defining RCM 49 established by an intersection of rotational axes of revolute joints 44 and end-effector 45 as known in the art of the present disclosure.

In practice, the structural arrangement of base 41, arms/arcs 43, revolute joint(s) 44, and end-effector 45 may be suitable for any interventional procedure or for particular interventional procedure(s).

Also in practice, base 41 has a structural configuration suitable for attachment to imaging platform 21 of acoustic probe 20 as will be exemplary described in the present disclosure. In one embodiment, base 41 may include a vertical translation joint 42a and/or a horizontal translation joint 42b for respectively vertically and/or horizontally translating end-effector 45 relative to device insertion port entry 23 of acoustic probe 20 while maintaining instrument device axis 48 extending through device insertion port 22 and RCM 49 located on axis 48 adjacent device insertion port exit 24.

Further in practice, interventional device(s) 60 include any type of interventional device suitable for being held by end-effector 45. Examples of interventional devices 60 include, but are not limited to, a biopsy needle, an ablation antenna, a spinal needle, an introducer and closure device and a mini-laparoscope. In one embodiment, end-effector 45 may therefore have a structural configuration suitable for holding particular interventional procedures. In another embodiment, robotic instrument guide 40 may include numerous changeable instrument device adapters 46 with each adapter 46 being structurally configured to accommodate different types of interventional device(s) 60 whereby end-effector 45 is reconfigurable to include any one of the adapters 46.

Also in practice, end-effector 45 may include an axis translation joint 47 to thereby translated end-effector 45 along instrument device axis 49 for controlling a depth of any interventional device 60 being held by end-effector 45 within a patient anatomy prepped for imaging by acoustic probe 20.

Still referring to FIG. 1, as known in the art of the present disclosure, a robotic instrument guide controller 50 of system 10 receives revolute joint data 52 informative of a pose of end-effector 45 within a workspace 51 encircling robotic instrument guide 40 whereby robotic instrument guide controller 50 may transition end-effector 45 between a plurality of poses within workspace 51.

In practice, one or all revolute joint(s) 44 may be motorized whereby robotic instrument guide controller 50 may communicate robotic actuation commands 53 to the motorized revolute joint(s) 44 for actuating the motorized revolute joint(s) 44 to transition end-effector 45 to a desired pose within workspace 51.

Also in practice, one or all revolute joint(s) 44 may be mechanical whereby robotic instrument guide controller 50 may issue robotic actuation data 54 to be displayed whereby an operator may manually actuate revolute joint(s) 44 to transition end-effector 45 to a desired pose within workspace 51.

Figure 4:
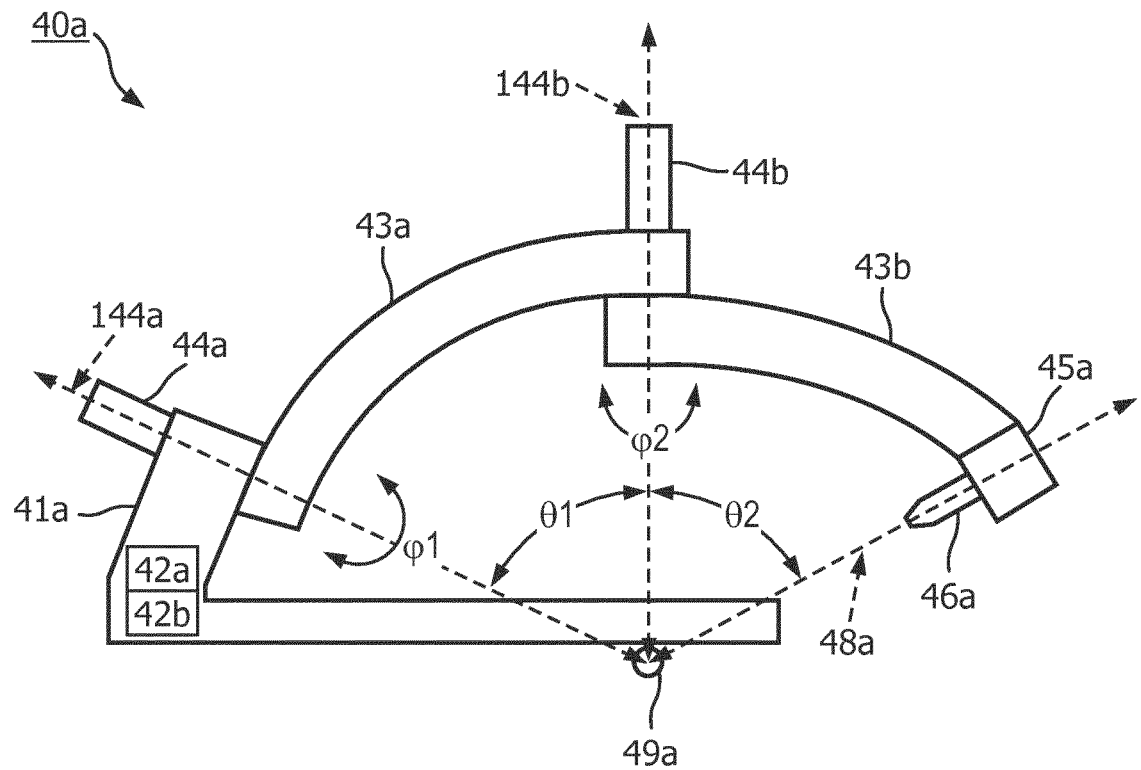
FIG. 4 illustrates an exemplary embodiment of a robotic instrument guide in accordance with the inventive principle of the present disclosure.
Figure 5A:
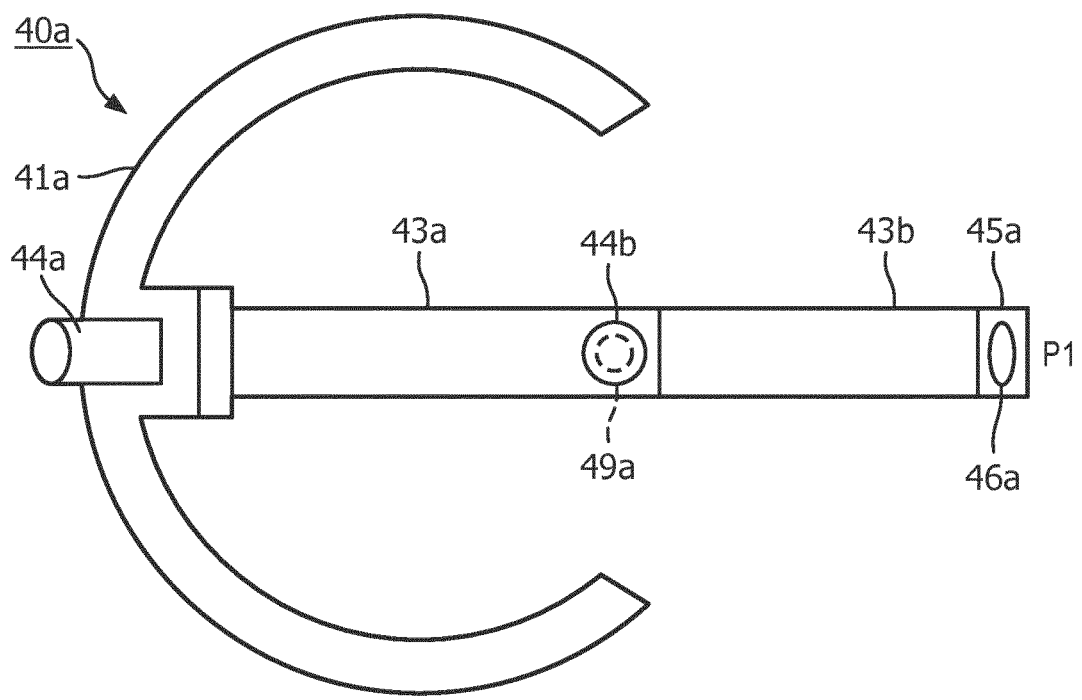
FIGS. 5A-5E illustrate top views of various poses of the robotic instrument guide of FIG. 4 in accordance with the inventive principle of the present disclosure
Figure 5B:
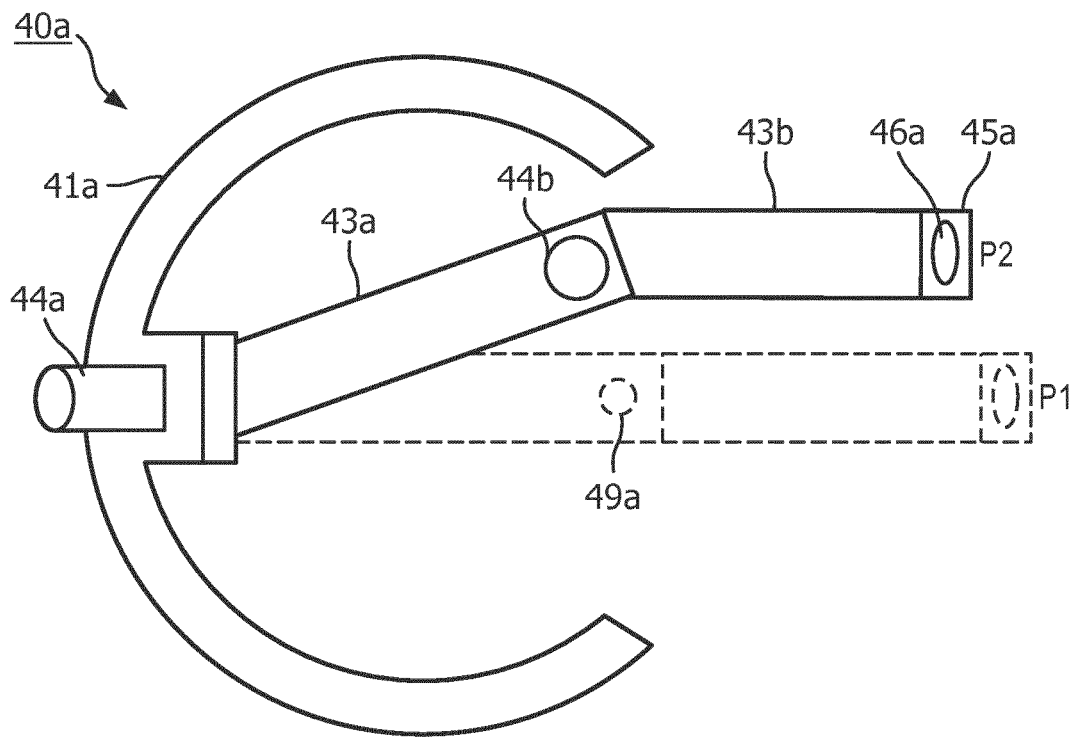
Figure 5C:
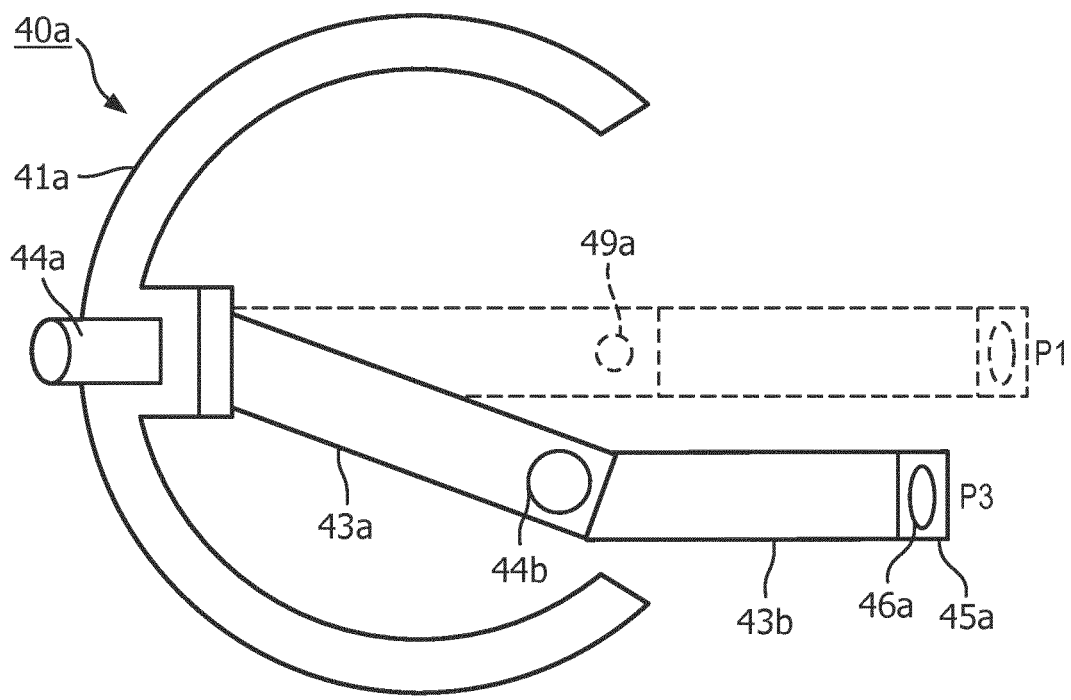
Figure 5D:
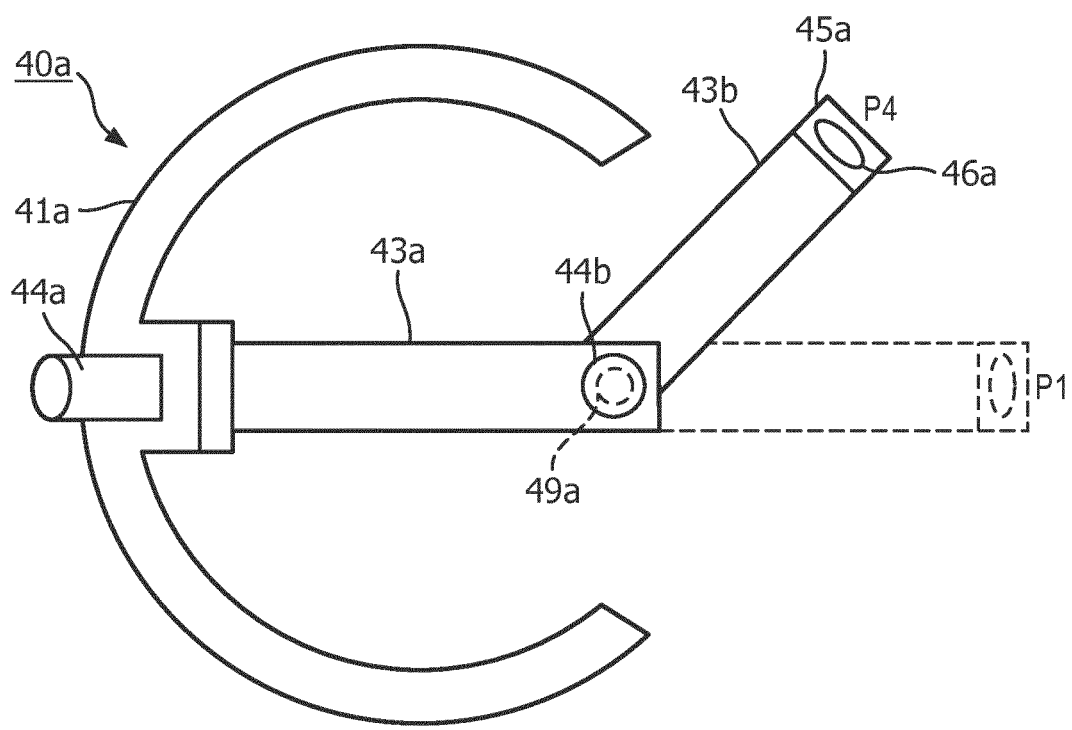
Figure 5E:
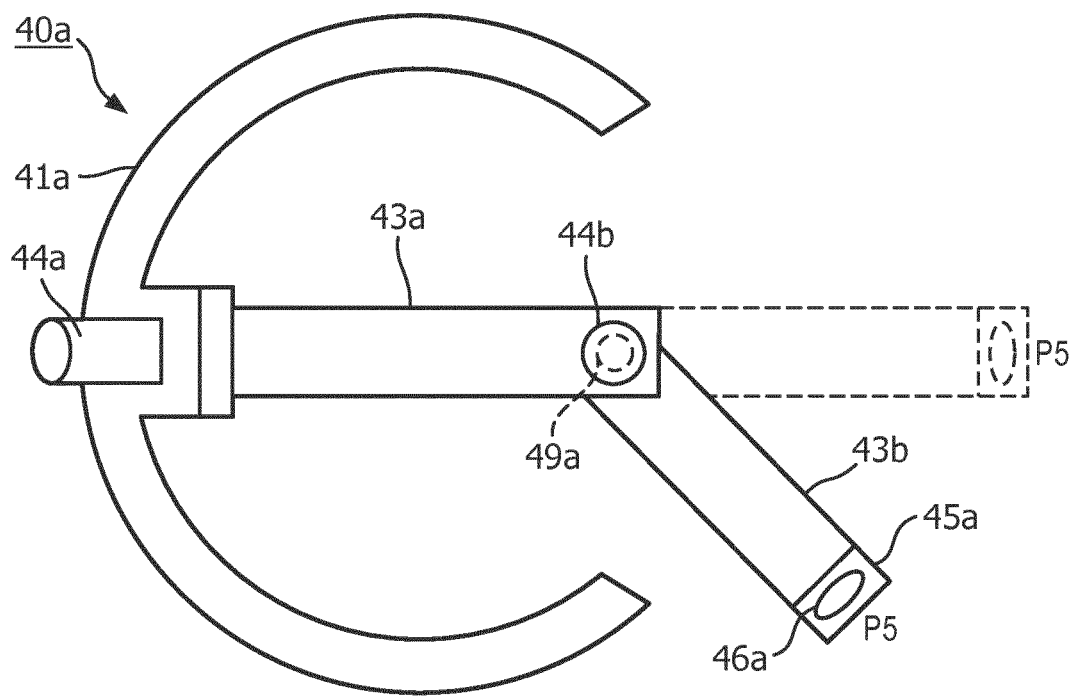

FIG. 4 illustrates an exemplary robotic instrument guide 40a employing a base 41a, a primary revolute joint 44a rotatable about a rotation axis 144a, a secondary revolute joint 44b rotatable about a rotation axis 144b, a support arc 43a, and an instrument arc 43b integrated with an end-effector 45a having an adapter 46a for holding an interventional device (not shown) along instrument device axis 48a. Support arc 43a is concentrically connected to revolute joint 44a and revolute joint 44b, and instrument arc 43b is concentrically connected to revolute joint 44b. More particularly, 1. rotational axes 144a, 144b and 48a intersect at a remote center of motion 49a of robotic instrument guide 40a,
2. a base arc length of $\theta_1$ of support arc 43a extends between rotation axes 144a and 144b,
3. an extension arc length $\theta_2$ of instrument arc 43b extends between rotation axis 144a and instrument device axis 48a,
4. an actuator, motorized or mechanical, of primary revolute joint 44a may be operated to co-rotate arcs 43a and 43b about rotation axis 144a for a desired $\varphi_1$ degrees to control a broad movement of end-effector 45a within a workspace between a plurality poses (poses P1-P3 shown in FIGS. 5A-5C respectively), and
5. an actuator, motorized or mechanical, of secondary revolute joint 44b may be operated to rotate instrument arc 43b about rotation axis 144b for a desired $\varphi_2$ degrees to control a targeted movement of end-effector 45a within the workspace between a plurality poses (poses P1, P4 and P5 shown in FIGS. 5A, 5D and 5E respectively)

As shown in FIG. 4, base 41a may incorporate vertical translation joint 42a (FIG. 1) and/or horizontal translation joint 42b (FIG. 1) to move remote center of motion 49a to a desired position relative to a device insertion port exit of an acoustic probe as previously described herein. Concurrently or alternatively, primary revolute joint 44a may incorporate a vertical translation joint and/or a horizontal translation joint to move remote center of motion 49a to a desired position relative to a device insertion port exit of an acoustic probe.

Referring back to FIG. 1, in one ultrasound guided interventional procedure embodiment of system 10, acoustic probe controller 30 and robotic instrument guide controller 50 cooperatively implement a robotic control of an interventional device 60 in view of volume ultrasound volumetric imaging by acoustic probe 20.

Generally, in execution of an interventional procedure, acoustic probe controller 30 generates ultrasound volumetric image data 34 informative of a volume ultrasound volumetric imaging of a patient anatomy based on echo data 33 received from the acoustic transducer array of acoustic probe 20 via a cable, and communicates ultrasound volumetric image data 34 to robotic instrument guide controller 50 whereby controller 50 generates robot actuation commands as needed to the revolute joints of robotic instrument guide 40 to actuate a motorized transition of end-effector 45a of robotic instrument guide 40 to a desired pose within the workspace, or generates robot actuation data 54 as needed for display to thereby provide information as to actuation of a mechanical transition of end-effector 45 of robotic instrument guide 40 to a desired pose within the workspace.

Figure 6:
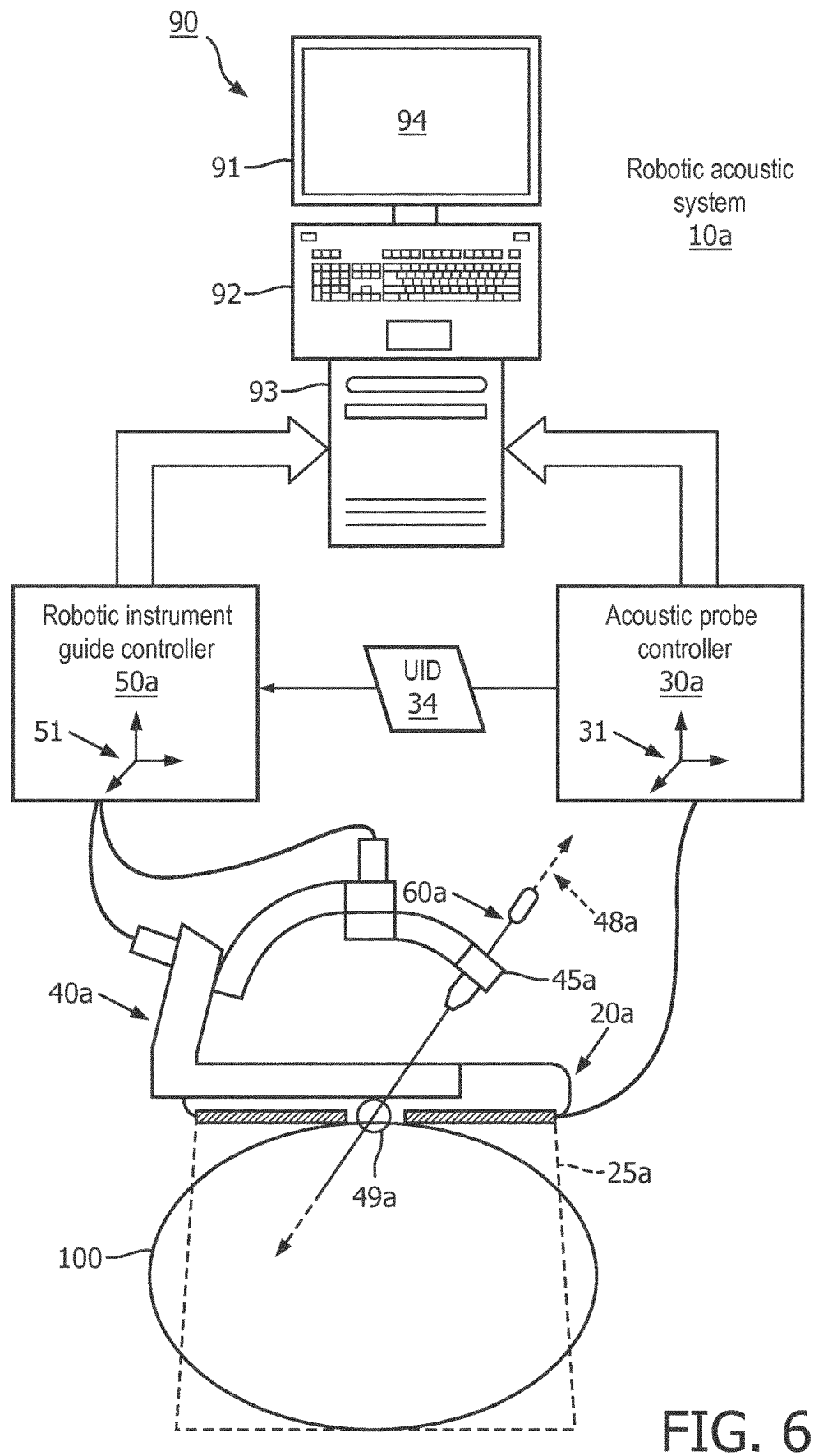
FIG. 6 illustrates an ultrasound guided exemplary embodiment of the robotic acoustic system of FIG. 1 in accordance with the inventive principles of the present disclosure.

FIG. 6 illustrates an exemplary ultrasound guided interventional procedure embodiment 10a of system 10.

Referring to FIG. 6, a workstation 90 includes an arrangement of a monitor 91, a keyboard 92 and a computer 93 as known in the art of the present disclosure.

An acoustic probe controller 30a and a robotic instrument guide controller 50a and are installed in computer 93, and each controller may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface.

The network interface may include one or more devices, as known in the art of the present disclosure or hereinafter conceived, for enabling communication with other hardware devices. In an non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent.

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage may further store one or more application modules in the form of executable software/firmware.

Alternatively, acoustic probe controller 30a and robotic instrument guide controller 50a may be integrated as installed on computer 93.

For this embodiment a first step of the interventional procedure as related to robotic acoustic probe of the present disclosure is an attachment of robotic instrument guide 40a to acoustic probe 20a in mounting position atop acoustic probe 20a. The attachment is enabled by unique clips or locks embedded in a substrate casing of acoustic probe 20a and self-adhesive tape. The use of unique clips provides for a position of robotic instrument guide 40a in respect to acoustic probe 20a, and therefore a mapping between ultrasound volumetric image space and the robotic workspace is known from a calibration of the robotic acoustic probe.

In practice, the calibration of the robotic acoustic probe may performed as known in the art of the present disclosure. For example, after the mounting, the following calibration steps may be performed:

First, controller 50a moves end-effector 45a holding a pointer tool to n position and acquires an end-effector position T (orientation and translation) calculated using forward kinematics.

Second, acoustic probe 20a is positioned on an ultrasound phantom (e.g., a gelatin medium) (not shown) whereby the tool is inserted into the ultrasound phantom by a certain depth in respect to previously acquired end-effector position T. If guide 40a provide a degree of freedom to control the insertion depth, the controller 50a uses the forward kinematics to obtain the tip of the end-effector 45a. Otherwise, an offset from the final end-effector position (translation) to the tip of the tool must be measured.

Third, controller 30a acquires position of the tool tip (p) segmented on an ultrasound volumetric image.

Fourth, the first three (3) steps are repeated, preferably more than three (3) iterations for higher accuracy, Fifth, controller 50a calculates a registration matrix using point-based registration method as known in the art of the present disclosure. The points utilized in the point-based registration include (1) acquired end-effector positions projected by the measured offset and the tool orientation axis and (2) target points segmented in the US image tool tip positions. If the insertion depth is actuated, then end-effector position may be directly utilized in the point-based registration.

Still referring to FIG. 6, upon calibration, acoustic probe 20a with a robotic instrument guide mounted thereon is positioned on a patient anatomy 100 whereby an acoustic coupling is assured by the practitioner firmly pushing acoustic probe 20a towards the patient skin.

Controller 30a is thereafter operated to control an ultrasound volumetric imaging of an organ or other inner structures containing the point of interest (e.g., a lesion). From the image, a target location is manually defined on the volume ultrasound volumetric image (e.g., a lesion location) or a target location is automatically segmented from the volume ultrasound volumetric image using the methods known in art of the present disclosure (e.g., a region-based segmentation, a thresholding segmentation, a model-based segmentation or a machine learning-based segmentation).

As soon as the target location is defined, an entry point of an interventional tool 60a (e.g., a needle) is constrained by a design of RCM 49a coinciding with the skin-entry point whereby controller 50a automatically moves end-effector 45a using robot kinematics to a pose for achieving a desired trajectory of interventional tool 60a into patient anatomy 100.

In one embodiment, controller 50a may implement a visual servoing technique as known in the art of the present disclosure. For example, the target location is user-selected or automatically selected within the volume ultrasound volumetric image user and controller 50a controls a transition of end-effector 45a to a pose for achieving a desired trajectory of interventional tool 60a into patient anatomy 100 by using a visual servoing that controls the pose of end-effector 45a relative to image features viewed by the endoscope. The position of the end-effector 45a in the ultrasound volumetric image space is known by controller 50a from the calibration process previously described above. This approach might be also applied to endoscopic procedures in which the laparoscope is hold by the instrument guide and the movement of the target on the laparoscopic image updates the position of the endoscope.

For this visual servoing, as the target location moves due to respiratory motion, controller 50a is able to adjust the pose of the end-effector by following the image features.

In another embodiment, the interventional procedure may require multiple device trajectories (e.g., radio-frequency ablation or irreversible electroporation may require multiple needle trajectories). Such procedures may be accomplished exclusive with volume ultrasound volumetric images, which are created for instance by stitching several single ultrasound volumes as known in the art of the present disclosure (e.g., a motorized sweeping of acoustic probe 20a over an imaging scene of patient anatomy 100. This may be achieved by tracking acoustic probe 20a by an external tracking device, or by using image-based registration methods as known in the art of the present disclosure.

More particularly, acoustic probe 20a is swept over a region of interest to thereby acquire several volume ultrasound volumetric images of the region of interest.

Next, controller 30a creates a compound image via an image-based image stitching of the volume ultrasound volumetric images as known in the art of the present disclosure.

Third, controller 30a controls a user defining of multiple trajectories on the compound image via monitor 91 as known in the art of the present disclosure. The user may also define objects to be avoided via the trajectories (e.g., ribs and vessels).

Fourth, acoustic probe 20a with guide 40a mounted thereto is moved over the same region of interest. This intraoperative volume ultrasound volumetric image is then registered by controller 50a to the compound image using a registration technique as known in the art of the present disclosure (e.g., a mutual-information-based registration).

As soon as acoustic probe 20a is positioned in a vicinity of one of the defined targets, controller 50a automatically adjusts an orientation of device 60a via an actuated movement of guide 40a (on-line adjustment).

Referring back to FIG. 1, in a second interventional procedure embodiment of system 10, acoustic probe controller 30, robotic instrument guide controller 50 and an imaging modality controller 72 of interventional imaging system 70 cooperatively implement a robotic control of an interventional device 60 in view of volume images generated by acoustic probe 20a and an imaging modality 71.

In practice, imaging modality 71 may be any imaging device of a stand-alone x-ray imaging system, a mobile x-ray imaging system, an ultrasound volumetric imaging system (e.g., TEE, TTE, IVUS, ICE), a computed tomography ("CT") imaging system (e.g., a cone beam CT), a positron emission tomography ("PET") imaging system and a magnetic resonance imaging ("MRI") system.

Generally, in execution of an interventional procedure, acoustic probe controller 30 generates ultrasound volumetric image data 34 informative of a volume ultrasound volumetric imaging of a patient anatomy based on echo signals 33 received from the acoustic transducer array of acoustic probe 20 via a cable, and communicates ultrasound volumetric image data 34 to robotic instrument guide controller 50. Concurrently, imaging modality controller 72 generates modality volumetric image data 73 informative of a modality volumetric imaging of a patient anatomy by the imaging modality 71 (e.g., X-ray, CT, PECT, MRI, etc.) and communicates modality volumetric image data 73 to robotic instrument guide controller 50. In response to the both data 34 and 73, controller 50a registers the ultrasound volumetric image (e.g., a single volume of a compound stitched volume) to the modality volumetric image by executing an image-based registration as known in the art of the present disclosure.

From the image registration, controller 50 generates robot actuation commands 53 as needed to the revolute joints 44 of robotic instrument guide 40 to actuate a motorized transition of end-effector 45 of robotic instrument guide 40 to a desired pose within the workspace, or generates robot actuation data 54 as needed for display to thereby provide information as to actuation of a mechanical transition of end-effector 45 of robotic instrument guide 40 to a desired pose within the workspace 51.

Figure 7:
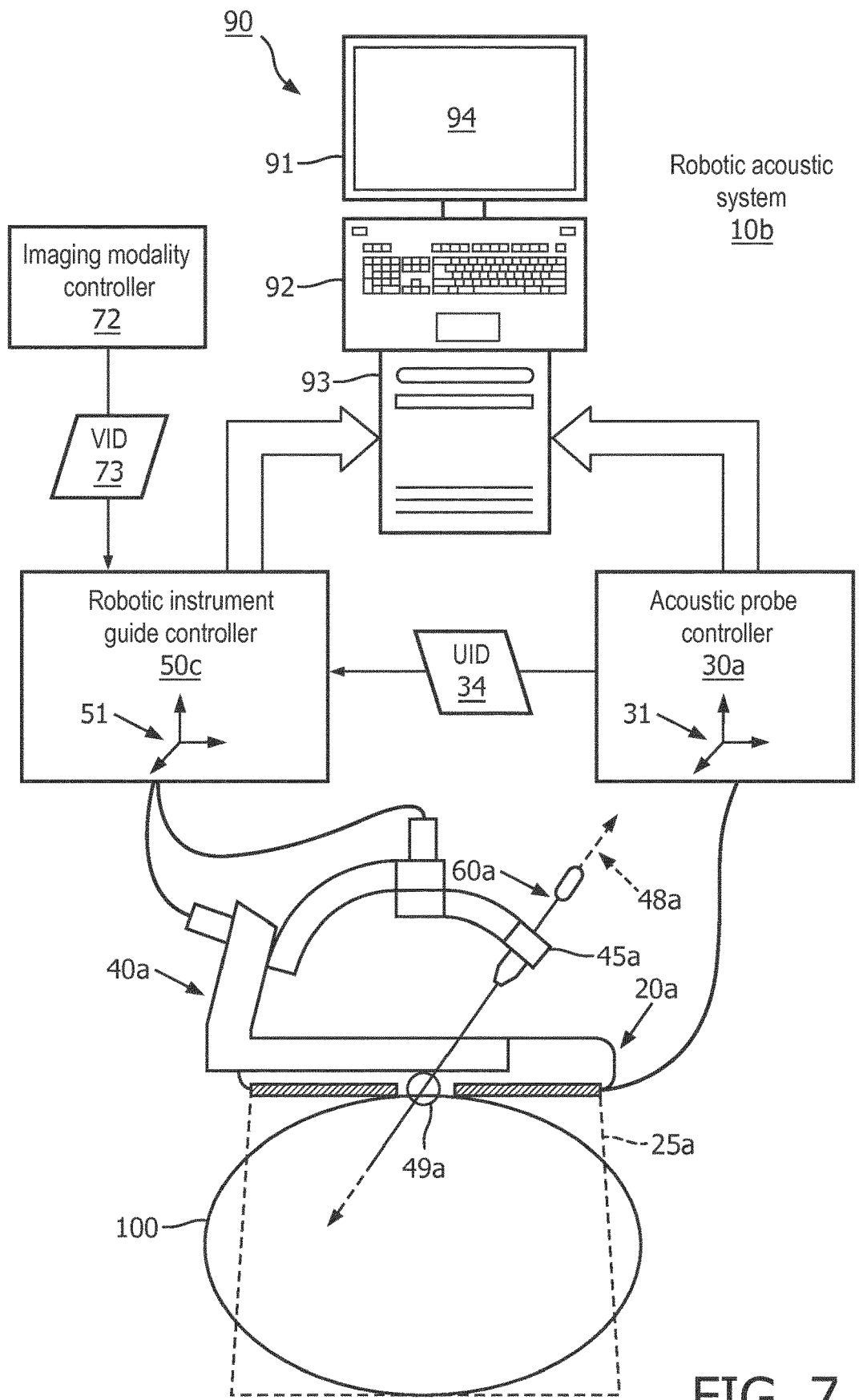
FIG. 7 illustrates a volume guided exemplary embodiment of the robotic acoustic system of FIG. 1 in accordance with the inventive principles of the present disclosure.

FIG. 7 illustrates an exemplary image modality guided interventional procedure embodiment 10b of system 10.

For this embodiment 10b, the imaging modality is an X-ray system and the revolute joints of robotic instrument guide 40a are mechanical, not motorized, whereby the motors are replaced by a locking mechanism (e.g. a clamp). When the locking mechanism is loosen, the arcs of guide 40a may be freely rotated as desired and the orientation of the end-effector 45a may therefore be adjusted. When the locking mechanism is tightened, the arcs of guide 40a are immobilized and device 60a being held by end-effector 45a is locked in a desired orientation. A feedback to a practitioner is provided from a robotic instrument guide 40a-to-CT image registration.

In one embodiment, the registration is performed using three (3) or more radio-opaque markers embedded in the non-movable base of guide 40a and includes the following steps.

First, guide 40a, individually or as mounted on acoustic probe 20a, is attached on to patient anatomy 100 via self-adhesive tape or any other attachment mechanism.

Second, a volumetric CBCT image of guide 40a as attached patient anatomy 100 is acquired by the X-ray system, and controller 72 communicates modality volumetric imaging data 73 informative of the volumetric CBCT image to controller 50c.

Third, controller 50c detects as least three (3) of the radio-opaque markers embedded in the non-movable base of guide 40a within the CBCT image to thereby identify a position of guide 40a in six (5) degree of freedom with respect to the patient anatomy 100 using a registration technique as known in the art of the present disclosure (e.g., a rigid point-based registration).

Fourth, controller 50c plans a trajectory of device 60a within patient anatomy 100 (e.g., a needle trajectory).

Fifth, controller 50a controls displayed feedback 94 on monitor 90 via an interface informative of required rotation angles on each joint in order to reach the desired device trajectory. The locking mechanism incorporates a scale to thereby assist the user in setting correct rotation angles of the arcs of guide 40a.

Finally, two (2) 2D fluoroscopy images of the same radio-opaque markers are acquired by the X-ray system and communicated to controller 50c, which registers the volumetric CBCT image to the 2D fluoroscopy images by determining a projection matrix for merging the 2D fluoroscopic images and volumetric CBCT image dependent on reference positions of the base of guide 40a via the markers to thereby merge said 2D fluoroscopic images with said preoperative 3D image using said projection matrix as known in the art of the present disclosure.

Referring back to FIG. 1, in a third interventional procedure embodiment of system 10, acoustic probe controller 30, robotic instrument guide controller 50 and a position tracking controller 80 of a position tracking system 80 cooperatively implement a robotic control of an interventional device 60 in view of a tracking of robotic instrument guide 40 by position tracking elements 81 of position tracking system 80.

In practice, position tracking elements 81 may include, but not be limited to, three (3) or more retro-reflective spheres, dots, electromagnetic sensors or lines, or optical fibers, etc. located on base 41 of guide 40 whereby a three-dimensional position of target feature may be calculated using triangulation techniques as known in the art.

Figure 8:
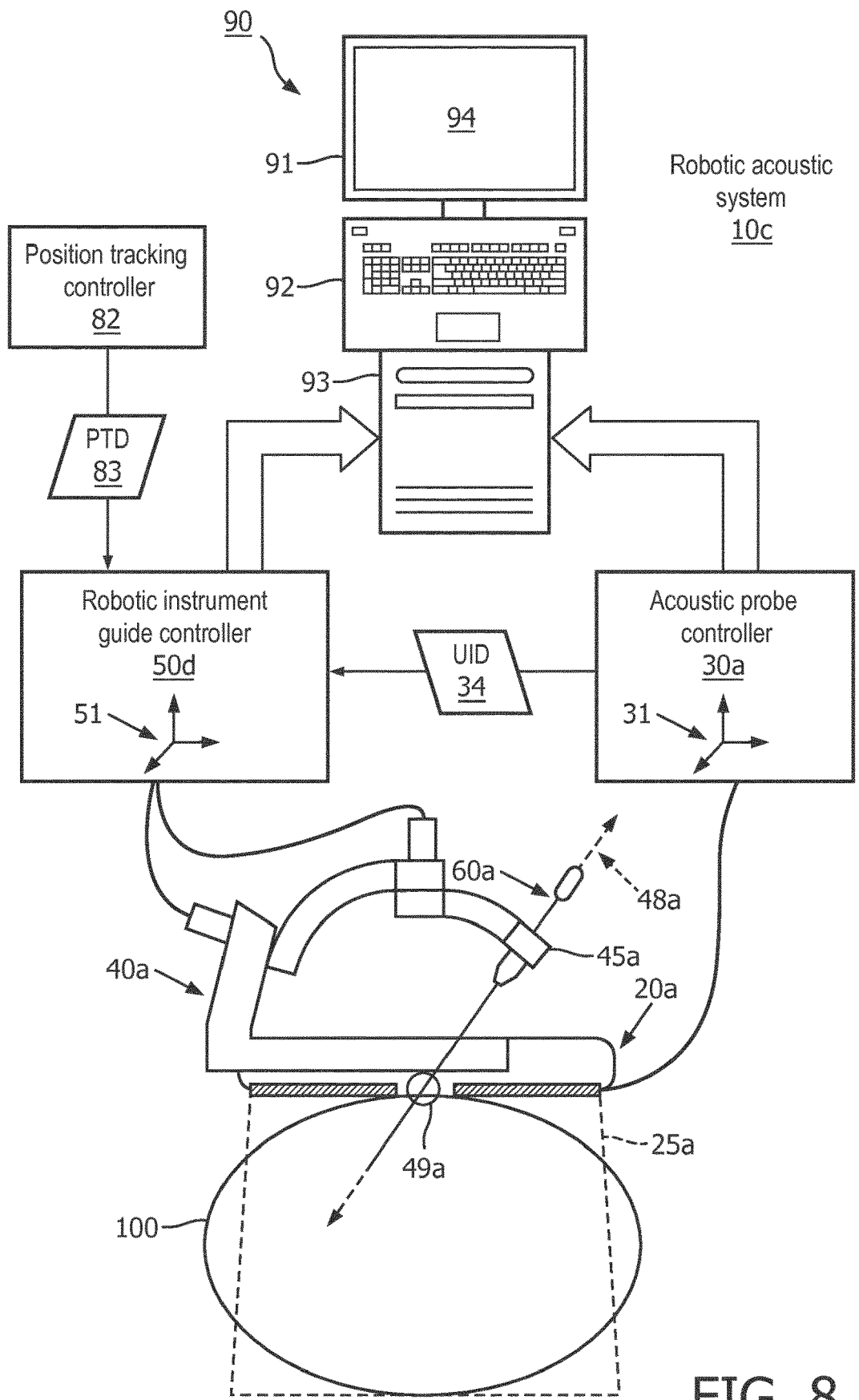
FIG. 8 illustrates a position tracking exemplary embodiment of the robotic acoustic system of FIG. 1 in accordance with the inventive principles of the present disclosure.

FIG. 8 illustrates an exemplary position tracking guided interventional procedure embodiment 10c of system 10.

For this embodiment 10c, position tracking controller 82 communicates position tracking data 83 informative of any tracked position of a base of guide 40a to robotic instrument guide controller 50d. In support of the interventional procedure, a calibration of the volume ultrasound volumetric image must be performed to facilitate subsequent tracking of the volume ultrasound volumetric image.

In one embodiment, particularly for an optical, electromagnetic or fiber tracking as guide trackers attached to the base of guider 40a, the calibration may be performed intraoperatively based on a position of each instrument guide tracker ($^{guide}T_{tracker}$) is known from the manufacturing process. The calibration matrix is calculated as in accordance with $^{guide}T_{image} = {}^{guide}T_{tracker} \cdot ({}^{image}T_{tracker})^{-1}$, where $^{image}T_{tracker}$ is calculated from features illustrated in the volume ultrasound volumetric image as known in the art of the present disclosure.

Referring to FIGS. 6-8, knowing an insertion depth on device 60a may be beneficial. In one embodiment, robotic instrument guide 40a has a $3^{rd}$ degree of freedom located at the end-effector as previously described within an axis translation joint 48a. This additional DOF controls the insertion depth of the needle and may be measured using an optical encoder embedded into the end-effector. Such an optical encoder can report the insertion depth with a sub-millimeter resolution.

In addition, having control over the insertion depth, an automatic instrument insertion using real-time image-based feedback may be performed. For example, ultrasound volumetric images and/or X-ray fluoroscopic images may be used to monitor the changes in the position of the target due to a breathing motion of patient anatomy 100 as previously described herein whereby device 60a (e.g., a needle) may be "shot" into patient anatomy in sync with a desired respiratory cycle.

Referring to FIGS. 1-8, those having ordinary skill in the art will appreciate numerous benefits of the present disclosure including, but not limited to, a robotic acoustic probe having a remote center of motion (RCM) locatable at a skin-entry point of a patient anatomy for more intuitive and safer interventional procedures Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive robotic acoustic probes and systems, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A robotic acoustic probe for application with an interventional device, the robotic acoustic probe comprising:
   an acoustic probe including:
      an imaging platform having a device insertion port defining a device insertion port entry and device insertion port exit, and
      an acoustic transducer array supported by the imaging platform and disposed relative to the device insertion port exit; and
   a robotic instrument guide including:
      (i) a base mounted to the imaging platform relative to the device insertion port entry, (ii) an end-effector transitionable between a plurality of poses relative to a remote-center-of-motion, the end-effector configured to hold the interventional device, and (iii) at least one arm coupling the base to the end-effector, wherein the end-effector defines an interventional device axis extending through the device insertion port, wherein the base includes at least one translation joint configured to translate the end-effector relative to the device insertion port, while maintaining the interventional device axis extending through the device insertion port, and wherein the remote-center-of-motion is a center of rotation located on the interventional device axis adjacent the device insertion port exit.

2. The robotic acoustic probe of claim 1, wherein the device insertion port is located in a center of the imaging platform.

3. The robotic acoustic probe of claim 1, wherein the imaging platform has a shape of a compact disc.

4. The robotic acoustic probe of claim 1, wherein the device insertion port tapers from the device insertion port entry to the device insertion port exit.

5. The robotic acoustic probe of claim 1, wherein the at least one translation joint is further configured to translate the remote-center-of-motion within a confined space adjacent the device insertion port exit.

6. The robotic acoustic probe of claim 1,
wherein the at least one arm includes:
a support arc, and
an instrument arc, wherein the end-effector is integrated with the instrument arc; and
wherein the robotic instrument guide further includes:
a primary revolute joint coupling the support arc to the base, and
a secondary revolute joint coupling the instrument arc to the support arc.

7. The robotic acoustic probe of claim 6,
wherein the primary revolute joint includes a primary motorized actuator; and
wherein the second revolute joint includes a secondary motorized actuator.

8. The robotic acoustic probe of claim 6,
wherein the primary revolute joint includes a primary mechanical actuator; and
wherein the second revolute joint includes a secondary mechanical actuator.

9. The robotic acoustic probe of claim 6,
wherein the end-effector is translatable relative to the instrument arc.

10. The robotic acoustic probe of claim 1,
wherein the end-effector includes an interventional device adapter.

11. A robotic acoustic system for application with an interventional device, the robotic acoustic system comprising:
an acoustic probe including:
an imaging platform having a device insertion port defining a device insertion port entry and device insertion port exit, and
an acoustic transducer array supported by the imaging platform and disposed relative the device insertion port exit; and
a robotic instrument guide including:
(i) a base mounted to the imaging platform relative to the device insertion port entry, (ii) an end-effector transitionable between a plurality of poses relative to a remote-center-of-motion within, the end-effector configured to hold the interventional device, and (iii) at least one arm coupling the base to the end-effector, wherein the end-effector defines an interventional device axis extending through the device insertion port, wherein the base includes at least one translation joint configured to translate the end-effector relative to the device insertion port, while maintaining the interventional device axis extending through the device insertion port, and wherein the remote-center-of-motion is a center of rotation located on the interventional device axis adjacent the device insertion port exit; and a robotic instrument guide controller structurally configured to control a transition of the end-effector between the plurality of poses relative to the remote-center-of-motion.

12. The robotic acoustic system of claim 11,
wherein the robotic instrument guide controller control of the transition of the end-effector between the plurality of poses relative to the remote-center-of-motion includes at least one of:
the robotic instrument guide controller being structurally configured to control a revolution of the end-effector about the remote-center-of-motion; and
the robotic instrument guide controller being structurally configured to control a translation of the end-effector along the interventional device axis.

13. The robotic acoustic system of claim 11, further comprising:
an acoustic probe controller structurally configured to control an ultrasound volumetric imaging of a patient anatomy by the acoustic transducer array; and
wherein the control by the robotic instrument guide controller of the transition of the end-effector between the plurality of poses relative to the remote-center-of-motion within a robot coordinate is derived from the ultrasound volumetric imaging of the patient anatomy by the acoustic transducer array.

14. The robotic acoustic system of claim 11, further comprising:
an interventional imaging system structurally configured to control a modality volumetric imaging of a patient anatomy by an imaging modality;
an acoustic probe controller structurally configured to control an ultrasound volumetric imaging of the patient anatomy by the acoustic transducer array; and
wherein the control by the robotic instrument guide controller of the transition of the end-effector between the plurality of poses relative to the remote-center-of-motion within a robot coordinate is derived from a registration between the modality volumetric imaging of the patient anatomy by the imaging modality and the ultrasound volumetric imaging of the patient anatomy by the acoustic transducer array.

15. The robotic acoustic system of claim 11, further comprising:
a position tracking processor structurally configured to control tracking of a robot pose of the end-effector relative to the remote-center-of-motion within a robotic coordinate system;

an acoustic probe controller structurally configured to control an ultrasound volumetric imaging of a patient anatomy by the acoustic transducer array; and wherein the control by the robotic instrument guide controller of the transition of the end-effector between the plurality of poses relative to the remote-center-of-motion within a robotic coordinate of the robotic coordinate system is derived from the tracking by the position tracking processor of the robot pose of the end-effector relative to the remote-center-of-motion within the robotic coordinate system.

16. An interventional method utilizing a robotic acoustic probe for an application with an interventional device, the method comprising:

providing an acoustic probe including:
an imaging platform having a device insertion port defining a device insertion port entry and device insertion port exit, and
an acoustic transducer array supported by the imaging platform and disposed relative the device insertion port exit;

providing a robotic instrument guide including:
(i) a base mounted to the imaging platform relative to the device insertion port entry,
(ii) an end-effector transitionable between a plurality of poses relative to a remote-center-of-motion, the end-effector configured to hold the interventional device, and
(iii) at least one arm coupling the base to the end-effector,
wherein the end-effector defines an interventional device axis extending through device insertion port,
wherein the base includes at least one translation joint configured to translate the end-effector relative to the device insertion port, while maintaining the interventional device axis extending through the device insertion port, and
wherein the remote-center-of-motion is a center of motion located on the interventional device axis adjacent the device insertion port exit;

positioning the robotic acoustic probe relative to a skin entry point of a patient anatomy, wherein the remote-center-of-motion coincides with the skin entry port; and subsequent to positioning the robotic acoustic probe relative to the skin entry point of the patient anatomy, at least one of:
ultrasound volumetric imaging the patient anatomy by the acoustic transducer array; and
transitioning the end-effector between the plurality of poses relative to the remote-center-of-motion.

17. The robotic acoustic method of claim 16,
wherein the transitioning of the end-effector between the plurality of poses relative to the remote-center-of-motion includes at least one of:
revolving the end-effector about the remote-center-of-motion; and
translating the end-effector along the interventional device axis.

18. The robotic acoustic method of claim 16,
wherein the transitioning of the end-effector between the plurality of poses relative to the remote-center-of-motion within a robot coordinate is derived from the ultrasound volumetric imaging of the patient anatomy by the acoustic transducer array.

19. The robotic acoustic method of claim 16, further comprising:
modality volumetric imaging the patient anatomy by an imaging modality,
wherein the transitioning of the end-effector between the plurality of poses relative to the remote-center-of-motion within a robot coordinate is derived from a registration between the modality volumetric imaging of the patient anatomy by the imaging modality and the ultrasound volumetric imaging of the patient anatomy by the acoustic transducer array.

20. The robotic acoustic method of claim 16, further comprising:
tracking a robot pose of the end-effector relative to the remote-center-of-motion within a robotic coordinate system,
wherein the transitioning of the end-effector between the plurality of poses relative to the remote-center-of-motion within a robotic coordinate of the robotic coordinate system is derived from the tracking by of the robot pose of the end-effector relative to the remote-center-of-motion within the robotic coordinate system.

* * * * *